(12) United States Patent
Barth et al.

(10) Patent No.: US 10,278,726 B2
(45) Date of Patent: May 7, 2019

(54) NAVIGATION AID FOR INTRODUCING AN ELONGATE MEDICAL PENETRATION ELEMENT INTO A PATIENT

(71) Applicant: SIEMENS AKTIENGESELSCHAFT, Munich (DE)

(72) Inventors: Karl Barth, Hoechstadt (DE); Rainer Graumann, Hoechstadt (DE); Gerhard Kleinszig, Forchheim (DE); Wei Wei, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 218 days.

(21) Appl. No.: 14/656,946

(22) Filed: Mar. 13, 2015

(65) Prior Publication Data

US 2015/0257849 A1 Sep. 17, 2015

(30) Foreign Application Priority Data

Mar. 13, 2014 (DE) .................. 10 2014 204 702

(51) Int. Cl.
*A61B 6/12* (2006.01)
*A61B 17/34* (2006.01)
(Continued)

(52) U.S. Cl.
CPC ...... *A61B 17/3403* (2013.01); *A61B 17/3468* (2013.01); *A61B 17/848* (2013.01);
(Continued)

(58) Field of Classification Search
None
See application file for complete search history.

(56) References Cited

U.S. PATENT DOCUMENTS 5,638,819 A * 6/1997 Manwaring .......... A61B 1/0005
600/424
6,473,489 B2 10/2002 Bani-Hashemi et al.
(Continued)

FOREIGN PATENT DOCUMENTS

DE 10049103 A1 7/2001
DE 102008021836 A1 11/2009

OTHER PUBLICATIONS

Navab, N. et al. "Camera Augmented Mobile C-Arm (CAMC): Calibration, Accuracy Study, and Clinical Applications" IEE Transactions on Medical Imaging. vol. 29, Jul. 2010 pp. 1412-1423.*

*Primary Examiner* — Michael J Carey
*Assistant Examiner* — Farouk A Bruce
(74) *Attorney, Agent, or Firm* — Laurence Greenberg; Werner Stemer; Ralph Locher

(57) ABSTRACT

A navigation aid for introducing an elongate medical penetration element into a patient. An X-ray image, containing a target region for the penetration element in a desired target position in a patient, is superimposed in alignment with video sequence images, containing at least in part the penetration element, to form a combination image sequence. The penetration element is captured in a start position and a desired penetration course of the penetration element at least to the target region of the penetration element in a desired target position, is visually displayed in the combination image sequence. A penetration element, such as a medical implant and/or instrument, in particular a K-wire (Kirschner wire), may carry a number of markers, such as additional bodies, coatings, elevations, and/or depressions, said markers altering a light reflection, are situated on and/or at and/or in the penetration element.

12 Claims, 2 Drawing Sheets

(51) Int. Cl.
  *A61B 17/84* (2006.01)
  *A61B 34/20* (2016.01)
  *A61B 90/00* (2016.01)
  *A61B 17/00* (2006.01)

(52) U.S. Cl.
  CPC .............. *A61B 34/20* (2016.02); *A61B 90/39* (2016.02); *A61B 2017/00119* (2013.01); *A61B 2034/2055* (2016.02); *A61B 2034/2057* (2016.02); *A61B 2090/363* (2016.02); *A61B 2090/364* (2016.02); *A61B 2090/365* (2016.02); *A61B 2090/376* (2016.02); *A61B 2090/3764* (2016.02); *A61B 2090/3937* (2016.02); *A61B 2090/3983* (2016.02)

(56) References Cited

U.S. PATENT DOCUMENTS

| | | | | |
|---|---|---|---|---|
| 2006/0173291 | A1* | 8/2006 | Glossop | A61B 90/96 600/424 |
| 2010/0076503 | A1* | 3/2010 | Beyar | A61B 17/1615 606/86 R |
| 2010/0312095 | A1* | 12/2010 | Jenkins | A61B 34/20 600/411 |
| 2012/0259204 | A1 | 10/2012 | Carrat et al. | |
| 2013/0006286 | A1* | 1/2013 | Lavelle | A61B 17/3468 606/185 |
| 2013/0197357 | A1* | 8/2013 | Green | A61B 8/0841 600/424 |

* cited by examiner

NAVIGATION AID FOR INTRODUCING AN ELONGATE MEDICAL PENETRATION ELEMENT INTO A PATIENT

CROSS-REFERENCE TO RELATED APPLICATION

This application claims the priority, under 35 U.S.C. § 119, of German patent application DE 10 2014 204 702.1, filed Mar. 13, 2014; the prior application is herewith incorporated by reference in its entirety.

BACKGROUND OF THE INVENTION

Field of the Invention

The invention relates to a method and a device for a navigation aid for introducing an elongate medical penetration element into a patient. Furthermore, the invention includes an elongate medical penetration element, in particular a medical implant and/or instrument, in particular a Kirschner wire (K-wire). Furthermore, the invention includes a computation and control unit and also an X-ray image capture and display unit for the navigation aid.

In interventions during emergency surgery, K-wires are usually used to bind and stabilize bone fragments of a patient. A known K-wire application can detect this K-wire in an X-ray image and visualize the desired penetration course thereof in the X-ray image. Surgeons can then alter and determine the orientation at the entry point on the basis of the detection result, such that an optimum path to the desired target position can be found. Owing to the restricted recording range of a C arm X-ray apparatus, it is often difficult to include the bone structures to be fixed and the K-wire simultaneously in an X-ray recording, especially at the patient's skin entry point. Moreover, after every actual target position or direction correction during the penetration process, the X-ray recording has to be repeated again in order to update the desired target position of the K-wire.

Apart from traditional navigation by means of a tracking system, at present there is no means of providing targeting assistance during the positioning of K-wires. The surgeon estimates the point of entry into the patient and the orientation of the K-wire on the basis of an X-ray recording. Afterward, the surgeon inserts the K-wire into the patient's bones according to said surgeon's experience and monitors the result, i.e. compares the actual target position with the desired target position. In the case of unsuccessful positioning, the K-wire is removed again via the penetration channel and repositioned. This iterative method has the consequence that if a plurality of attempts are made, bone material is destroyed, hence implants are not afforded sufficient support and the result of the operation is not optimal.

In the prior art described above, therefore, an identification of the position and orientation of the medical implants and/or instruments takes place exclusively in the X-ray image, as does the display of the penetration course of the implants and/or instruments.

SUMMARY OF THE INVENTION

It is accordingly an object of the invention to provide a navigation aid for elongate medical penetration elements, and in particular medical implants and/or instruments, and a corresponding method which overcome the above-mentioned and other disadvantages of the heretofore-known devices and methods of this general type and which provides for the insertion and implanting into the patient with the highest possible quality, i.e. with the least possible deviation from a planned desired target position.

With the foregoing and other objects in view there is provided, in accordance with the invention, a method of aiding a navigation during an introduction of an elongate medical penetration element into a patient. The method includes at least the steps listed below.

The method includes a step of providing video sequence images containing at least in part the penetration element are provided.

The method includes a step of providing at least one X-ray image containing at least one target region for the penetration element in a desired target position in the patient.

The method also includes a step of superimposing the at least one X-ray image in alignment with the video sequence images to form a combination image sequence thereby capturing the penetration element in a start position and, proceeding from the start position, visually displaying in the combination image sequence a desired penetration course of the penetration element at least as far as the target region of the penetration element in the desired target position.

In other words, the method according to the invention for navigation aid for introducing an elongate medical penetration element into a patient is distinguished by the following aspects. At least one X-ray image, containing at least one target region of the penetration element in a desired target position in a patient, is superimposed, in particular in real time or quasi-real time, in alignment with 2D/3D video sequence images. The 2D/3D video sequence images contain at least in part the penetration element, to form a combination image sequence. The penetration element is captured in a start position and, proceeding from the latter, a desired penetration course (also designated as trajectory or path curve, as a so-called "augmented reality" (AR)) of the penetration element at least as far as the target region of the penetration element in a desired target position, is visually displayed in the combination image sequence.

The expression "capturing the penetration element" in this case is taken to mean detecting the 2D or 3D longitudinal extent of the penetration element, in particular the imaginary center line thereof.

As the "start position" of the penetration element, it is possible in this case to choose an arbitrary position before the introduction of the penetration element into the patient, or upon contact of the penetration element with the patient's skin, or after the introduction of the penetration element into the patient. Therefore, in the start position, the penetration element may not yet have penetrated or else may have already penetrated a way into the patient. In the start position, however, the penetration element must be situated at least partly in the region of the video sequence images.

The terms "desired penetration course" and "actual penetration course" are understood to mean the following:

In a first case, it is possible for the desired penetration course to be defined at the beginning of the method once in a prognostic manner and thereafter no longer to be altered or to be altered only a few times (e.g. two, three, four times). The desired penetration course could thus correspond to a medical ideal penetration course which the penetration element is intended to follow with the highest possible accuracy. If no deviation, or deviation only to a permissible degree, is made from this prognosticated ideal penetration course, only the actual penetration course corresponds approximately to the desired penetration course. However, if an impermissible deviation is made from this prognosticated ideal penetration course, then countermeasures can be implemented, such as e.g. an alarm being output, which will be described in even greater detail later. In this first case, therefore, the desired penetration course is defined just once at the beginning of the method and thereafter is no longer changed or is only changed slightly a few further times.

In a second case, it is possible for the desired penetration course to change more or less continually and to be continually updated at an arbitrary frequency corresponding e.g. to the image refresh frequency of the video sequence images. Thus, at the beginning of the method, the desired penetration course could correspond to a medical ideal penetration course which the penetration element is intended to follow with the highest possible accuracy. During the introduction of the penetration element into the patient, the desired penetration course is then continually adapted to the actual penetration course, such that the actual penetration course always corresponds approximately to the desired penetration course to a permissible degree. It is only at a low updating frequency of the desired penetration course or at a low image refresh frequency of the video sequence images of e.g. less than 1 Hz (1 frame per second) that it would then be possible for the actual penetration course then to deviate to an impermissible degree from the currently relevant, continually updating desired penetration course. Countermeasures can then in turn be implemented, such as e.g. an alarm being output, which will be described in even greater detail later. In this second case, therefore, the desired penetration course is defined at the beginning of the method and thereafter updated continually further times by means of the actual penetration course. Therefore, if a relatively high, e.g. customary image refresh frequency of 24, 48, 50 or 100 Hz is used, then the desired penetration course can be updated, e.g. likewise 24, 48, 50 or 100 times per second. Thus, a harmonic movement of the actual and desired penetration courses is made possible and an impermissible deviation of the actual penetration course from the desired penetration course is virtually ruled out. In other words, if the actual penetration course is altered in comparison with the old desired penetration course, the new updated desired penetration course changes as well.

Of course, any arbitrary combination of the two cases mentioned above can also be used in the method according to the invention.

The term "video sequence images" should be understood here to mean arbitrary image sequences which can be used to detect a movement of an object captured by the video images, independently of how many images are made or displayed per unit time. In other words, by way of example, a sequence of individual still images can also be involved here. Preferably, however, the image sequence is fast enough that real-time observation of the moved object is possible.

By means of the method according to the invention corresponding image data can be made available even when a plurality of elongate medical penetration elements are introduced into the patient all at once, wherein said penetration elements can be introduced into the patient in parallel and/or serially with respect to one another.

The penetration elements can remain in the patient as implants for a relatively long time or even permanently or else can be introduced into the patient as an instrument for just a relatively short time for diagnosis and/or therapy purposes and can be removed again.

A first X-ray image is created before the penetration of the penetration element into the patient. One or a plurality of further X-ray images can then be created during the penetration and/or in the target position of the penetration element, in order to monitor the actual penetration course and, if appropriate, to redefine the desired penetration course of the penetration element.

The combination image sequence can represent a pure superimposing addition of the X-ray image with the video sequence images, or else a superimposing addition of the X-ray image with only the image excerpt of the video sequence images which do not overlap the X-ray image, that is to say lie outside the X-ray image.

According to the invention, therefore, the position and orientation (2D or 3D vector) of the medical implants and/or instruments, in particular K-wires, are identified in the video sequence images, the penetration course of the implants and/or instruments being displayed at least in the region of interest in the X-ray image, if appropriate in the entire X-ray image and/or additionally also in the video sequence images of the combination image.

What is advantageous in this case is that significantly fewer (ideally one, max, two) X-ray images have to be created for implanting the implants and/or instruments and a lower radiation dose in comparison with the prior art is therefore introduced into patients. The navigation aid is usable even if an image region of an X-ray image, comprising a region of a target position of the implants and/or instruments in the patient, lies outside a penetration entry region of the implants and/or instruments into the patient, as may be the case e.g. with C arm X-ray apparatuses.

Moreover, an impermissible deviation of the actual penetration course of the penetration element from the desired penetration course can be identified very simply and rapidly by virtue of the insertion of the desired penetration course into the combination image sequence. This can prompt the operating surgeon, if appropriate, to make corrections by at least partly retracting the penetration element and redefining the desired penetration course.

The device according to the invention for navigation aid for introducing an elongate medical penetration element into a patient comprises:

a first display unit for visually displaying a combination image sequence composed of at least one X-ray image and video sequence images, wherein the at least one X-ray image, containing at least one target region of the penetration element in a desired target position in a patient, is superimposed in alignment with video sequence images, containing at least in part the penetration element, to form a combination image sequence, a capture unit for capturing the penetration element in a start position, comprising e.g. a CCD camera, a calculation unit for calculating a desired penetration course of the penetration element proceeding from the start position as far as a target region of the penetration element in a desired target position, a second display unit for visually displaying the desired penetration course of the penetration element proceeding from the start position at least as far as the target region of the penetration element in a desired target position, in the combination image sequence displayed by the first display unit.

The first display unit for displaying a combination image sequence and the second display unit for visually displaying the desired penetration course of the penetration element in this case utilize the same display element, e.g. the monitor (which is present in any case) of the C arm X-ray apparatus, or else a separate monitor in the vicinity of the patient couch.

The penetration element according to the invention is embodied in particular as a medical implant and/or instrument, in particular as a K-wire, wherein a number of markers, in particular in the form of coatings and/or elevations and/or depressions and/or additional bodies, said markers altering a light reflection, are situated on and/or at and/or in the penetration element. Of course, the additional bodies themselves can likewise comprise coatings and/or elevations and/or depressions. Moreover, all combinations of the above mentioned embodiments of the markers are protected within the scope of the present invention.

The K-wire, which consists of metal at least on the outer side, is intended to be detected in the video image in particular in real time. The trajectory of the K-wire is subsequently visualized in an X-ray image. However, the detection of the K-wire can be disturbed by the ambient lighting. Therefore, optical marker spheres are preferably used in order to stabilize the detection of the K-wire. The spheres can be fitted (in particular not fixed) for example such that the imaginary longitudinal axis of the K-wire runs through the center of all the spheres. The marker spheres should be readily visible only in the video image sequence.

Furthermore, a computation and control unit for use in the method is protected, for the calculation and partly automated control of the desired penetration course of the penetration element before and/or during the penetration of the penetration element into the patient. This can be carried out e.g. by means of a CNC-controlled manipulator, wherein preferably at least one of the parameters, penetration direction, penetration advance or penetration depth of the penetration element is not automated by the control.

The dependent claims and the further description contain particularly advantageous configurations and developments of the invention, wherein in particular the claims of one category can also be developed analogously to the claims of one of the other categories and features of different exemplary embodiments can also be combined among one another in order to form new variants of the invention.

One preferred embodiment of the method comprises the fact that the desired target position is also visually displayed in the combination image sequence. Consequently, very simply and rapidly, an impermissible deviation of the actual target position of the penetration element from the desired target position can be identified and, if appropriate, a correction by at least partly retracting the penetration element and redefining the desired target position can thus be prompted.

In this case, the X-ray image and the video sequence images can at least partly overlap or adjoin one another. In the extreme case, the X-ray image and the video sequence images need not even overlap at all, even if this should be an exceptional case.

In particular, by means of appropriate orientation of the X-ray image or of the X-ray recording apparatus, the point of entry of the penetration element into the patient's skin lies in the video sequence images and the point of entry of the penetration element into the bone or the first bone fragment lies in the X-ray image. Consequently, the operating surgeon, on the monitor, can move to the skin entry point of the penetration element and then insert the penetration element as far as the first bone fragment and, on the monitor, can observe a possible deflection of the penetration element upon screwing into the first bone fragment and, if appropriate, can make a correction. Alternatively, however, it is also possible for both points of entry of the penetration element into the skin and into the bone to lie both in the video sequence images and in the X-ray image. However, the penetration element is only ever visible to the operating surgeon in the video sequence images, but not in the X-ray image created initially in the operation. It is only if, during the introduction of the penetration element into the patient or in its actual target position, one or a plurality of X-ray images must be created again that the penetration element would then be visible there as well.

One advantageous embodiment comprises the fact that in the case of an impermissible deviation of an actual penetration course or an actual target position of the penetration element from the desired penetration course or from the desired target position, the actual penetration course or the actual target position is displayed in the combination image sequence and/or an acoustic and/or optical alarm is output. Consequently, the operating surgeon can make a course correction or end position correction of the penetration element in a timely manner, if appropriate, without the need for further X-ray images of the region of interest in the patient.

One alternative embodiment comprises the fact that control commands for a manipulator for controlling the penetration element are generated in a partly automated manner before and/or during the penetration of the penetration element into the patient. Consequently, one or two or more of the parameters, direction, advance or depth of the penetration of the penetration element can be implemented in a machine-controlled manner, e.g. by means of CNC control of a manipulator, wherein preferably one of the parameters is always implemented by the operating surgeon him or herself.

In particular, the penetration element can comprise at least one medical implant and/or instrument. The method according to the invention is suitable in particular for image support for a K-wire (Kirschner wire) as penetration element, since the latter has to be used for carrying out fast treatment, e.g. of a comminuted fracture after an accident, with the highest possible precision, without the patient being subjected to an excessively high X-ray radiation burden.

The method according to the invention is therefore suitable particularly for a C arm X-ray apparatus, since only very small excerpts of an X-ray image can be created by means of the X-ray source arrangement of said apparatus. Alternatively, however, the method according to the invention can also be used in CT apparatuses and/or other 2D or 3D X-ray apparatuses, if necessary.

In this case, the video sequence images are created by means of a video camera, in particular CCD video camera, which is arranged on the C arm X-ray apparatus and/or CT apparatus and/or other 2D or 3D X-ray apparatus and is registered with the X-ray source arrangement, for example, in accordance with the following patent specifications: U.S. Pat. No. 6,473,489 B2; U.S. Pat. No. 6,447,163 B1; U.S. Pat. No. 6,229,873 B1; U.S. Pat. No. 6,227,704 B1; and their German counterpart DE 10049103 B4 (i.e., the image data of the X-ray apparatus and the video sequence images are registered on one another).

Particularly if a penetration element that is metallically lustrous on the surface is used, as preferred embodiments for the penetration element it is appropriate that a number of markers, in particular in the form of coatings and/or elevations and/or depressions and/or additional bodies, said markers being visible at least in the video sequence image and altering light reflection, are situated on and/or at and/or in the penetration element. The light reflection of the penetration element can thereby be altered in such a way that the penetration element can be identified better for the video camera and more precise positioning and navigation of the penetration element can thus be performed. Of course, coatings and/or elevations and/or depressions can alternatively or additionally also be present on the additional bodies. In particular regular bodies such as e.g. spheres, cubes, pyramids, etc. are appropriate as additional bodies since they can be identified identically from a plurality of spatial directions and entail a simple and very accurate calculation of the position, orientation and movement of the penetration element.

In order that the penetration element can be kept as short as possible, preferably the additional bodies lie on and/or at and/or in the penetration element fixedly in a cohesive and/or positively locking manner or displaceably in a force-locking/friction-locking manner axially at least counter to the penetration direction. Consequently, when the penetration element is introduced into the patient's body, the additional bodies are wiped toward the rear on the surface of the patient, but still remain for further positioning and navigation tasks on the penetration element. However, it is also possible for some or all of the additional bodies to be wiped off completely from the penetration element in the course of penetration. If the markers are accommodated within the penetration element, then the penetration element must, of course, be embodied as transparent or translucent at least at these locations, in order that the markers can also be identified by the video camera. However, wiping off the inner markers from the penetration element is then rather not necessary, but indeed also possible if the penetration element is embodied as a hollow body, such as e.g. in the case of a catheter, an endoscope or a hollow needle.

In particular, however, at least two markers spaced apart from one another are present on the penetration element and at least one of the markers is arranged in the region of the proximal end of the penetration element, whereas the other marker, at least prior to introduction into the patient, has been or is arranged as far away as possible from the first marker.

In one development, the penetration element itself could be equipped with actively luminous elements as markers, such as LEDs, for example, which can be removed again from the patient after implantation has been carried out.

Other features which are considered as characteristic for the invention are set forth in the appended claims.

Although the invention is illustrated and described herein as embodied in a navigation aid for introducing an elongate medical penetration element into a patient, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings. The FIGURE is generally not to scale.

DETAILED DESCRIPTION OF THE INVENTION

Figure 1:
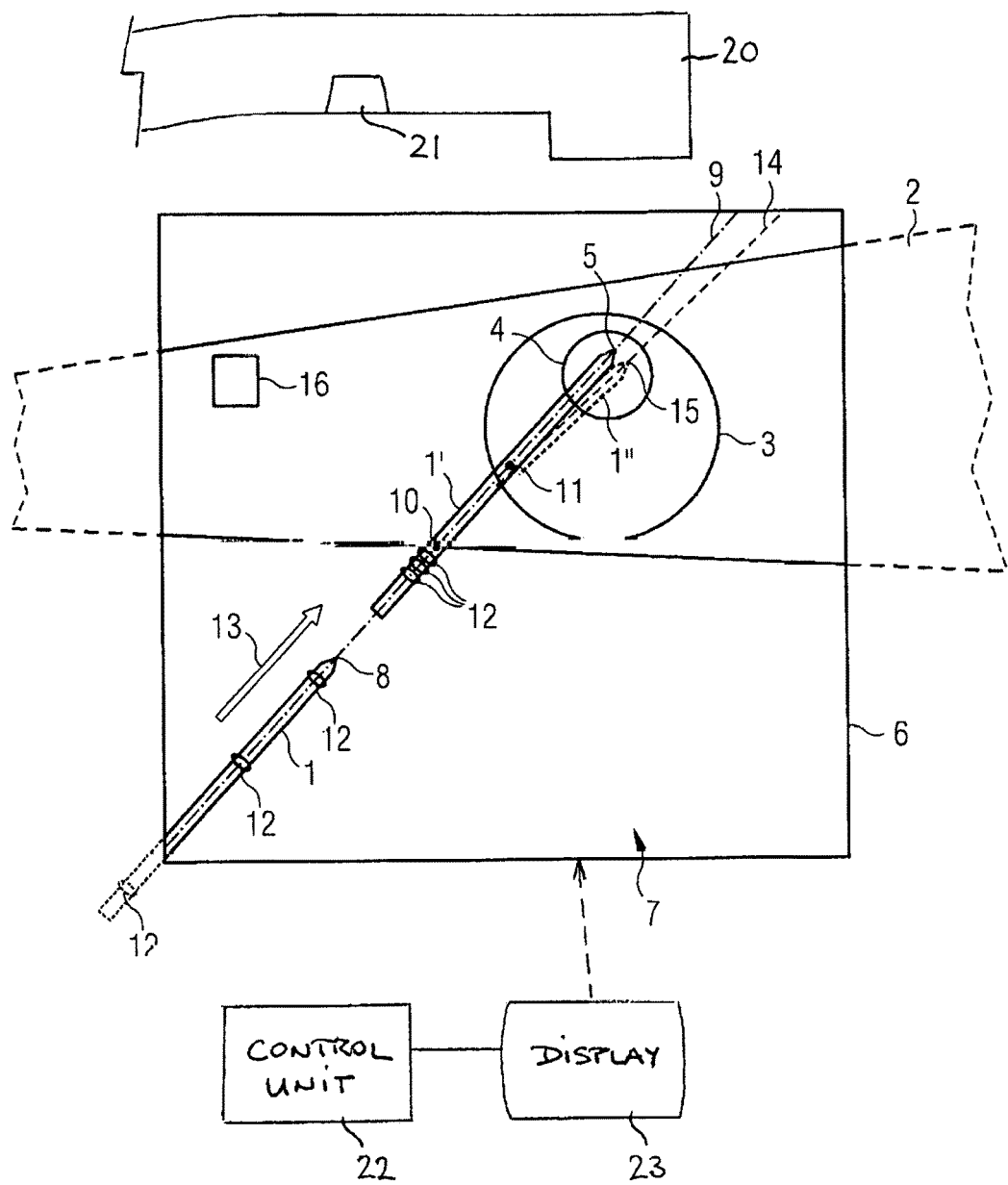
FIG. 1 shows a navigation aid according to the invention for introducing an elongate medical penetration element into a patient.

Referring now to the FIGURE of the drawing in detail, there is shown a part of a leg of a patient 2. The patient is lying on a non-illustrated operating table for the purpose of an operation on defective bones.

An optical augmented reality (AR) marker 16 has been or is being fitted to the surface of the skin of the patient 2, e.g. by being adhesively bonded there. The AR marker 16 can be identified by a video image sequence and a movement of the patient can thus be "tracked." If the movement of the patient 2 deviates impermissibly from a predefined magnitude of a patient parameter, this can be identified by means of the AR marker 16 and transferred to a control unit 22 for issuing an alarm.

First, an X-ray image 3 of a patient 2 is produced, e.g. shortly before the operative intervention, e.g. by means of a C arm X-ray apparatus 20. The X-ray image 3 contains at least one target region 4 of interest in the patient 2. Following application, a desired target position 5 of a K-wire 1' that has penetrated into the patient 2 is then intended finally to be located in said target region 4 in the patient 2.

Afterward, video sequence images 6 are created by means of a (CCD) video camera 21, for example. The sequence images 6 include at least in part the K-wire 1, e.g. in the start position 8 thereof.

Although the reference line of the start position 8 is directed to the tip of the K-wire 1, it is intended to represent the start position of the entire K-wire 1, that is to say to include at least information about an imaginary longitudinal straight line (in particular center line) through at least two points on the K-wire 1, such that the 2D or 3D longitudinal extent (direction or orientation) of the K-wire is thus identified.

The K-wire 1 in the start position 8 need not necessarily lie totally outside the patient 2, but rather can already be situated on or partly in the patient 2, e.g. in position 10 or 11. The start position 8 can therefore be chosen arbitrarily, but the K-wire 1 must always be situated at least partly in the region of the video sequence images 6, in order that it can be detected by the video camera.

The camera for the video sequence images 6 can be activated e.g. after the starting of navigation software.

Afterward, the X-ray image 3 and the video sequence images 6 are displayed in a superimposed fashion as a combination image sequence 7 on a monitor of the C arm X-ray apparatus or on a separate display.

Since the K-wire 1 usually consists of metal at least on the surface, said K-wire, under the strong OP lighting required, can be identified by the camera only with very great difficulty owing to the unfavorable light reflection, which would lead to inaccuracies in the determination of the actual position and the calculation of the desired penetration course 9 of the K-wire 1.

In order to improve this disadvantage, here three spherical markers 12 are pushed on the K-wire 1 in a friction-locking manner, such that a first marker 12 becomes located distally, a second marker 12 approximately medially and a third marker 12 proximally relative to the penetration direction 13 of the K-wire 1. However, the markers 12 can also be omitted or fewer or more than three markers 12 can be used. If markers 12 are necessary, ideally only two markers 12 at the start and end of the K-wire 1 will be necessary.

The spherical markers 12 have surfaces which have an identical appearance from all spatial directions. Moreover, the markers 12 have an effect of altering the light reflection, such that they are better visible to the video camera. This can be effected by means of suitable coatings and/or elevations and/or depressions of the markers 12 themselves, or else, with omission of the additional bodies as markers 12, by means of suitable coatings and/or elevations and/or depressions of the K-wires 1 themselves. Arbitrary combinations thereof are also possible.

The navigation software then calculates, on the basis of the start position 8 of the K-wire 1, said start position being determined with the aid of the markers 12, the desired penetration course 9 of said K-wire and, if appropriate, also the desired target position 5 of said K-wire and indicates it/them in the combination image sequence 7 in real time or quasi-real time. The quasi-real time can have a time delay of a few ns, µs, ms, seconds or even minutes in comparison with real time itself. Of course, the combination image sequence 7 can be stored if appropriate also with the inserted desired penetration course 9 and if appropriate also its desired target position 5 of the K-wire 1 in a memory e.g. of a computation and control unit of the C arm X-ray apparatus and can be retrieved again as required.

A process of applying the K-wire 1 will now be briefly described in greater detail with reference to the FIGURE, which process can be accompanied with image assistance by the invention.

The initial situation is the created combination image sequence 7 with inserted desired penetration course 9 and if appropriate also its desired target position 5 of the K-wire 1.

The K-wire 1 is already situated at the start position 8 or else is moved there manually or by means of an, if appropriate, CNC-controlled, manipulator. Three marker spheres 12 spaced apart from one another sequentially in the penetration direction 13 are situated on the K-wire 1.

Proceeding from said start position 8, the K-wire 1 is then moved along the simulated line of the desired penetration course 9, said line being displayed in the combination image sequence 7, in the direction of the surface of the body of the patient 2 until the tip of the K-wire 1 reaches an entry point 10 on the skin of the patient 2. Proceeding from said entry point 10, the K-wire 1 is then moved further, under somewhat increased expenditure of force, along the line of the desired penetration course 9 though the tissue of the patient 2 as far as an entry point 11 of a first bone or bone fragment. In this case, the front most marker 12 gets left on the outside of the patient's skin and slides on the K-wire 1 counter to the penetration direction 13 in the direction of the central marker 12.

Proceeding from the bone entry point 11, the K-wire 1 is then screwed further into the bone by means of a rotary drive situated outside the patient, as far as possible without leaving the line of the desired penetration course 9. Of course, the K-wire 1 can also already be turned outside and in the soft tissue of the patient 2.

In this case, the central marker 12 also gets left on the outside of the patient's skin and slides on the K-wire 1 counter to the penetration direction 13 in the direction of the rear marker 12 at the end of the K-wire 1. All three markers 12 then become located on the outside of the surface of the skin of the patient 2 one behind another, whereby it is possible to ascertain the actual penetration course 14 and the actual target position 15 of the K-wire 1" in the combination image sequence 7.

Ideally, on its passage through the bones or bone fragments of the patient 2, the K-wire 1 does not deviate all that much from the ideal desired penetration course 9, and so the K-wire 1 then finds its desired target position 5 in the target region 4 with sufficiently low tolerance, and is provided with the reference sign 1' there in the FIGURE. Finally, if appropriate, a last (if appropriate second) X-ray image 3 is also created for final monitoring.

However, if the K-wire 1, on its actual penetration course 14, deviates from the ideal line 9 to an undesirable extent, as indicated e.g. by dashed lines with the actual target position 15 and the K-wire 1", then temporally before or at the latest upon reaching the actual target position 15, it is possible for an acoustic and/or optical alarm to be output, such that the user can then retract the K-wire a little and easily readjust the direction of the K-wire 1 and thus of the desired penetration course 9. Thus, further X-ray images need not be created either on the actual penetration course 14 or in the actual target position 15, which results in a very low total radiation dose for the patient 2 during the operation.

Overall, it is then normally necessary to produce just two X-ray images 3, one before (for the purpose of determining the desired penetration course 9) and one after (for the purpose of final monitoring of the actual target position 15) the application of the K-wire 1 into the patient 2.

All the above mentioned positions and courses can, of course, also be ascertained and calculated as 3D data from 2D raw data of a plurality of X-ray and/or video sequence images from different spatial directions, as required. As a rule, however, 2D X-ray images and 2D video sequence images suffice for generating the combination image sequence 7 and the simulated desired penetration course 9 of the K-wire 1.

For the sake of completeness, it is also pointed out that the use of the indefinite article "a" or "an" does not preclude the fact that the relevant features can also be present in plural form. Likewise, the term "unit" does not preclude the fact that the latter can consist of a plurality of components, which if appropriate can also be spatially distributed.

Figure 2:
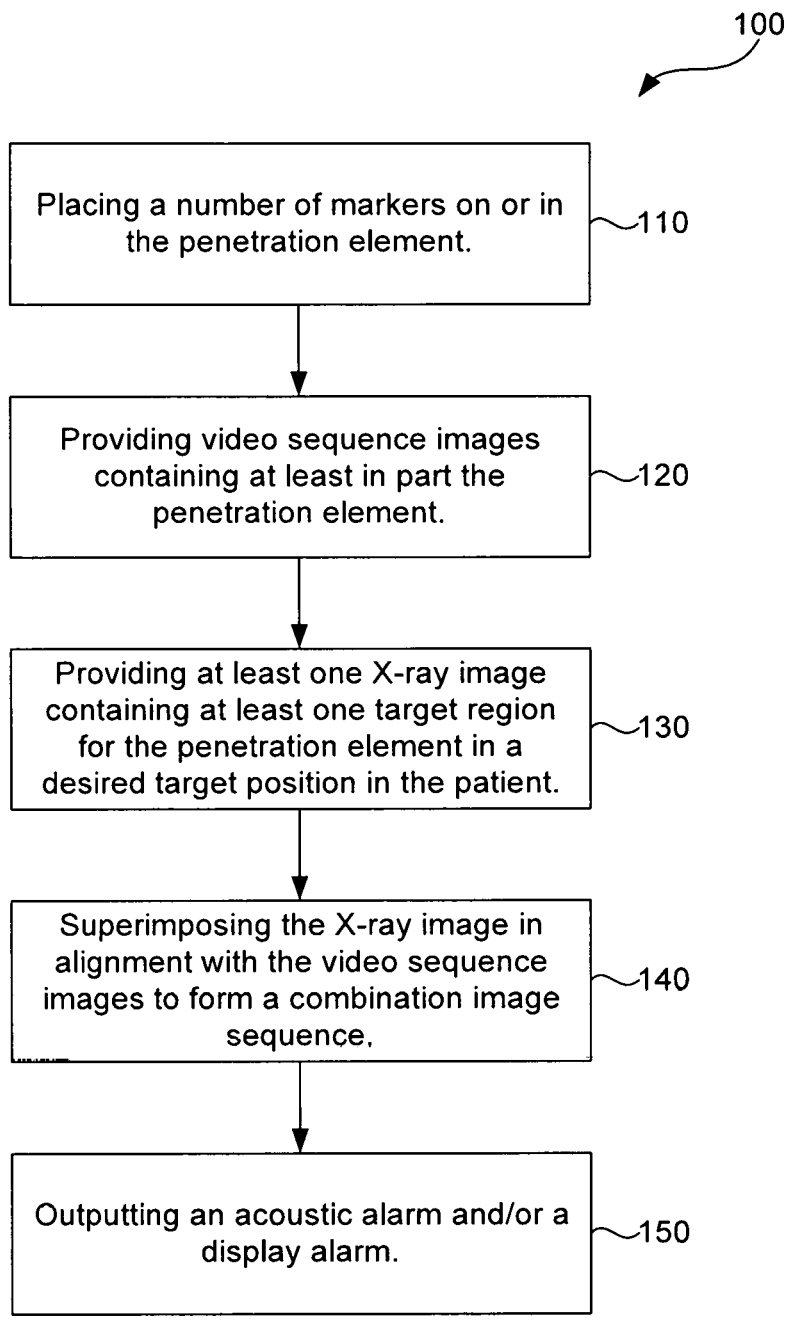
FIG. 2 is a flow chart showing basic steps of the method.

FIG. 2 is a flow chart showing the basic steps of the method 100 of aiding a navigation during an introduction of an elongate medical penetration element into a patient includes the following step. Step 110 includes placing a number of markers on or in the penetration element. Step 120 includes providing video sequence images containing at least in part the penetration element. The video sequence images can be created with a video camera disposed on the C-arm X-ray apparatus. Step 130 includes providing at least one X-ray image containing at least one target region for the penetration element in a desired target position in the patient. Step 140 includes superimposing the X-ray image in alignment with the video sequence images to form a combination image sequence. The formed combination image sequence captures the penetration element in a start position. The formed combination image sequence also, proceeding from the start position, visually displays a desired penetration course of the penetration element at least as far as the target region of the penetration element in the desired target position. Step 150 includes; on occasion of an impermissible deviation of an actual penetration course or an actual target position of the penetration element from the desired penetration course or from the desired target position, outputting an acoustic alarm and/or a displayed alarm.

The following is a summary list of reference numerals and the corresponding structure used in the above description of the invention:

1 Penetration element in start position
1' Penetration element in desired target position
1" Penetration element in actual target position
2 Patient
3 X-ray image
4 Target region
5 Desired target position
6 Video sequence images
7 Combination image sequence 8 Start position
9 Desired penetration course
10 Point of entry into the patient's skin
11 Point of entry into the patient's first bone
12 Marker
13 Penetration direction
14 Actual penetration course
15 Actual target position
16 AR marker for patient tracking
20 C-arm X-ray unit
21 Video camera
22 Control unit
23 Display

The invention claimed is:

1. A method of aiding a navigation during an introduction of an elongate medical penetration element into a patient, the method comprising:
    slidably attaching a plurality of optical markers to the penetration element such that the plurality of optical markers slide on the penetration element to remain visible outside the patient as the penetration element is introduced into the patient;
    obtaining, from a camera, video sequence images containing at least in part the penetration element, wherein the plurality of optical markers are visible in the video sequence images;
    obtaining, from an x-ray apparatus, at least one X-ray image containing at least one target region for the penetration element in a desired target position in the patient;
    superimposing the at least one X-ray image in alignment with the video sequence images to form a combination image sequence which captures the penetration element in a start position and, which proceeding from the start position, visually displays a desired penetration course of the penetration element at least as far as the target region of the penetration element in the desired target position and displaying the combination image sequence on a display;
    with a control unit, ascertaining an actual penetration course of the penetration element in the combination image sequence based on a location of at least the part of the penetration element in the video sequence images; and
    on occasion of an impermissible deviation of the actual penetration course from the desired penetration course in the combination image sequence, outputting an acoustic alarm from the control unit.

2. The method according to claim 1, wherein the combination image sequence shows the desired target position of the penetration element.

3. The method according to claim 1, wherein the X-ray image and the video sequence images at least partly overlap or adjoin one another.

4. The method according to claim 1, further comprising, on occasion of the impermissible deviation of the actual penetration course or the actual target position of the penetration element from the desired penetration course or from the desired target position, displaying the actual penetration course or the actual target position in the combination image sequence.

5. The method according to claim 1, further comprising controlling the penetration element in a partly automated manner before and/or during the penetration of the penetration element into the patient.

6. The method according to claim 1, wherein the penetration element comprises at least one medical implant.

7. The method according to claim 1, wherein the penetration element is a K-wire (Kirschner wire).

8. The method according to claim 1, wherein the X-ray image is created by a C-arm X-ray apparatus comprising at least one X-ray source arrangement.

9. The method according to claim 8, further comprising creating the video sequence images with a video camera disposed on the C-arm X-ray apparatus, wherein the video camera is registered with the at least one X-ray source arrangement.

10. A navigation aid device for introducing an elongate medical penetration element into a patient, the device comprising:
    the penetration element, wherein the penetration element includes a plurality of optical markers slidably attached to the penetration element such that the plurality of optical markers slide on the penetration element to remain visible outside the patient as the penetration element is introduced into the patient;
    a first display unit for visually displaying a combination image sequence composed of at least one X-ray image and video sequence images, wherein the plurality of optical markers are visible in the video sequence images, wherein the at least one X-ray image, containing at least one target region of the penetration element in a desired target position in a patient, is superimposed in alignment with video sequence images, containing at least in part the penetration element, to form a combination image sequence;
    a capture unit for capturing the penetration element in a start position;
    a calculation unit for calculating a desired penetration course of the penetration element proceeding from the start position as far as a target region of the penetration element in a desired target position;
    a second display unit for visually displaying the desired penetration course of the penetration element proceeding from the start position at least as far as the target region of the penetration element in a desired target position, in the combination image sequence displayed by the first display unit; and
    a control unit configured for ascertaining an actual penetration course of the penetration element in the combination image sequence based on a location of the penetration element in the video sequence images;
    said control unit configured for outputting an acoustic alarm on occasion of an impermissible deviation of the actual penetration course of the penetration element from the desired penetration course in the combination image sequence.

11. The navigation aid device according to claim 10, wherein the penetration element is configured as a medical implant.

12. The navigation aid device according to claim 10, wherein the penetration element is configured as a K-wire.

* * * * *